US012521278B2

(12) United States Patent
Hertel

(10) Patent No.: US 12,521,278 B2
(45) Date of Patent: Jan. 13, 2026

(54) PASSIVE VENTED GOGGLE

(71) Applicant: HEATWAVE VISUAL, Gilroy, CA (US)

(72) Inventor: Justin Marc Hertel, Gilroy, CA (US)

(73) Assignee: HEATWAVE VISUAL, Gilroy, CA (US)

( * ) Notice: Subject to any disclaimer, the term of this patent is extended or adjusted under 35 U.S.C. 154(b) by 0 days.

(21) Appl. No.: 18/354,334

(22) Filed: Jul. 18, 2023

(65) Prior Publication Data

US 2025/0025345 A1 Jan. 23, 2025

(51) Int. Cl.
*A61F 9/02* (2006.01)

(52) U.S. Cl.
CPC .............. *A61F 9/028* (2013.01); *A61F 9/026* (2013.01); *A61F 9/027* (2013.01)

(58) Field of Classification Search
CPC .......... A61F 9/028; A61F 9/026; A61F 9/027; A61F 9/02
See application file for complete search history.

(56) References Cited

U.S. PATENT DOCUMENTS 6,637,038 B1 * 10/2003 Hussey .................. A61F 9/028 2/436
2004/0105070 A1 * 6/2004 Hockaday ............... A61F 9/028 2/452
2006/0059608 A1 * 3/2006 Difilippo ................. A61F 9/028 2/436
2006/0119948 A1 * 6/2006 Matsumoto ............... A61F 9/02 359/624
2009/0300830 A1 * 12/2009 Mage ...................... A61F 9/025 2/452
2011/0296596 A1 * 12/2011 Chen ....................... A61F 9/028 2/436
2015/0074880 A1 * 3/2015 Blanchard ............. G02C 5/008 2/431
2015/0374550 A1 * 12/2015 Saylor ..................... A61F 9/028 2/436
2018/0071145 A1 * 3/2018 Lee ......................... A61F 9/028
2020/0093643 A1 * 3/2020 Young ..................... A61F 9/025

* cited by examiner

*Primary Examiner* — Uyen T Nguyen
(74) *Attorney, Agent, or Firm* — Schwegman Lundberg & Woessner, P.A.

(57) ABSTRACT

The invention pertains to a vented goggle that optimizes air circulation to enhance user comfort and mitigate fogging. Key features include a frame that houses a lens and has both an inlet and an outlet for airflow, with a channel connecting the two. The frame's exterior surface faces away from the user, while its interior surface contacts the user's face. A vented cover can be incorporated on the outlet, and liner material may be applied to the interior surface or inner periphery of the frame for enhanced comfort. Multiple pairs of inlets and outlets can be included for superior ventilation. A removable insert forms a duct in the channel and also serves as an attachment point for a goggle strap. The design offers improved performance and comfort in a variety of environments and activities.

7 Claims, 7 Drawing Sheets

PASSIVE VENTED GOGGLE

BACKGROUND

The invention relates generally to the field of sports and protective eyewear, including goggles. In particular, the invention relates to managing airflow within and through a goggle frame.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
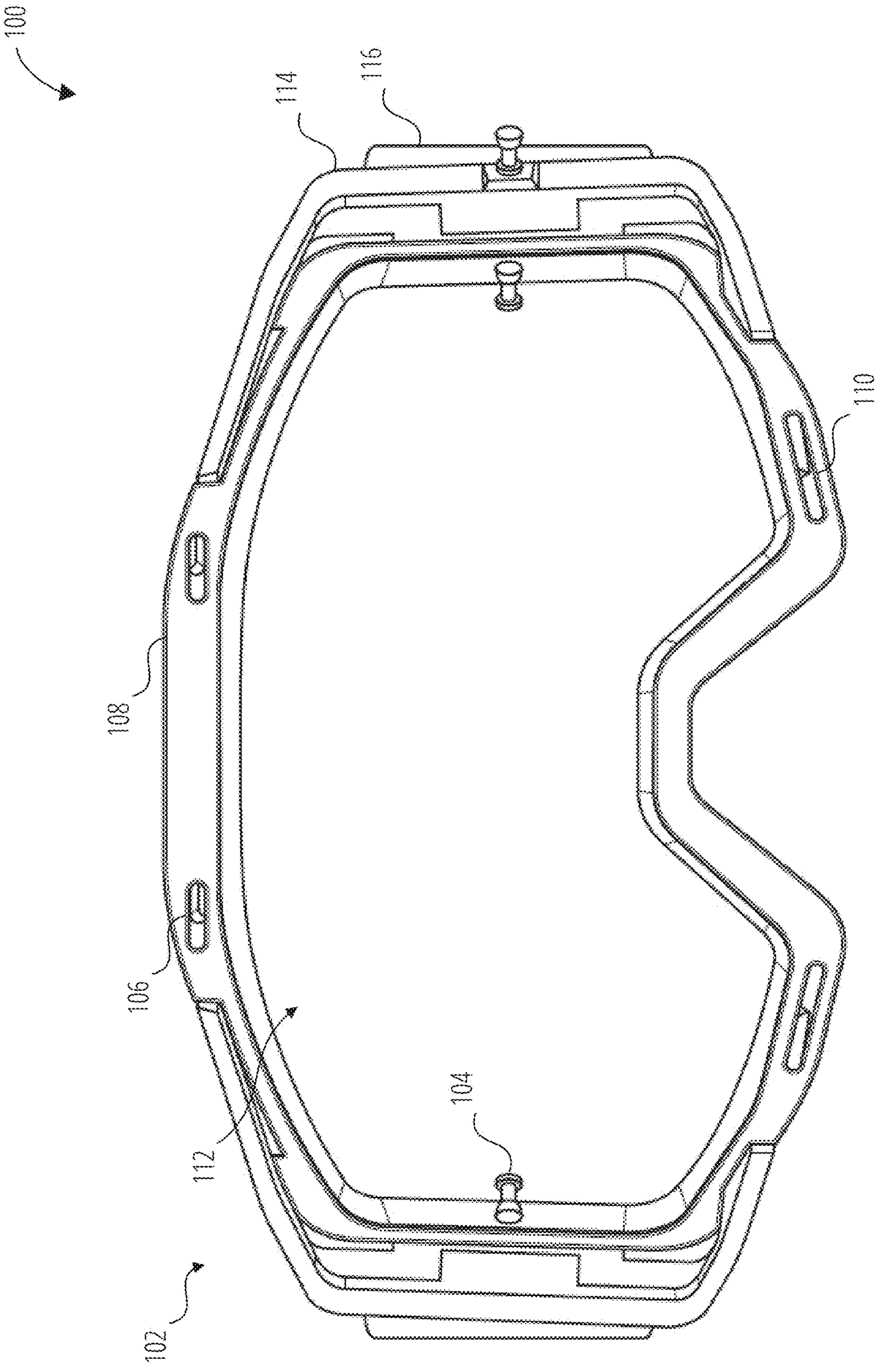
FIG. 1 is a diagram of a passively vented goggle, in accordance with one embodiment.

Example embodiments described herein have several features, no single one of which is indispensable or solely responsible for their desirable attributes. Without limiting the scope of the claims, some of the advantageous features will now be summarized. While the features and structures are described below in connection with embodiments of eyewear, such as eyeglasses and goggles, it is to be understood that the features and structures can be implemented in any head-worn device which supports one or more lenses in the wearer's field of view. For example, other head-worn supports may include, but are not limited to helmets; face masks; balaclavas; and breaching shields. According to certain embodiments, the invention disclosed herein relates to a system for air-circulation in the context of head-worn devices to avoid fogging, and ensure user comfort.

In various exemplary embodiments, a goggle is provided that comprises a frame that comprises a lens aperture, an exterior surface, an interior surface, and an inner periphery, the inner periphery being located between the exterior surface and the interior surface, the exterior surface being configured to be oriented away from a user's face, and the interior surface being configured to be oriented upon the user's face. The goggle may include a lens mounted upon the exterior surface of the frame and within the lens aperture of the frame, wherein the frame is disposed at least partially around an outer periphery of the lens. The exterior surface of the frame may include one or more inlets, wherein the one or more inlets are connected to corresponding channels that extend to one or more outlets disposed upon the inner periphery of the frame, and behind the lens. For example, the inlets may be arranged along various positions of the exterior periphery of the frame.

According to certain example embodiments, the outlet includes a cover, such as a block-off plug, or in some embodiments vented cover. For example, in some embodiments, the cover may comprise an arranged of a set of vent holes, wherein the vent holes may comprise one or more openings, and wherein the openings are arranged randomly or in a pattern along the surface of the cover. The openings may comprise circular openings, slats, or openings of any other shape. In some embodiments, the opening may comprise a manipulable valve, wherein a user of the goggle may turn the valve to open or close the opening, thereby increasing or decreasing airflow through the channel. In some embodiments, the vented cover may be removable, such that a user of the goggle may remove the vented cover entirely, to maximize airflow through the channel.

In an embodiment of the invention, the outlet may include a foam insert that fits within the outlet, and may be held in place by the outlet cover, by one or more barbs or protrusions along the outlet's peripheral surface, or by a suitable adhesive. In some embodiments, the foam inserts may be interchangeable, such that a user of the goggle may select a foam insert having a foam density suitable for their environment or need. For example, a user may select a first foam insert having a higher density for environments with fine dust, or similarly a lighter density foam insert in cleaner environments, to provide greater airflow to the user.

In some embodiments, the goggle may further comprise a liner material applied upon one or both of the interior surface and inner periphery of the frame, wherein the liner material is configured to conform to a shape of a surface (i.e., a wearer's face). The liner material may be comprised of foam, or other compressible material. For example, in certain embodiments, the liner material may overlap or cover the outlet disposed upon the inner periphery of the frame, such that air flowing through the channel and out of the outlet must pass through a portion of the liner material.

In some embodiments, the frame may comprise a slotted mount to retain an insert, wherein the insert may comprise an outrigger to mount a strap for the goggle. For example, the slotted mount may be disposed upon on the outer surface of the frame, such that the insert may be pressed into the slotted mount. In some embodiments, the channel may comprise a duct formed by a surface of the insert and the exterior periphery of the frame.

In some embodiments, the goggle includes provisions to facilitate the attachment and removal of thin, transparent tear-off layers (i.e., "tear-offs"), providing users with the ability to maintain clear vision in the face of dust, mud, or other debris, without the need to remove or manually clean the goggles. For example, the goggles may include a tear-off attachment system, wherein the tear-off attachment system comprises one or more protrusions, such as posts, which project outward from the frame, or through the lens and are adapted to hold tear-off layers.

Each tear-off is a thin, transparent sheet, generally shaped to correspond to the lens of the goggles and including holes that align with the posts of the tear-off attachment system. Accordingly, to attach a tear-off, a user aligns the holes in the tear-offs with the posts and slips the tear-off onto the posts. Multiple tear-offs can be stacked, allowing the user to remove the topmost tear-off when it becomes obscured, revealing a clean tear-off underneath. In some embodiments, the posts of the tear-off attachment system may have a secondary locking mechanism to ensure tear-offs stay securely in place during rigorous activity, wherein the mechanism can be disengaged when the user is ready to remove a tear-off.

Reference will now be made in detail to specific example embodiments for carrying out the inventive subject matter of the present disclosure. In the following description, specific details are set forth in order to provide a thorough understanding of the subject matter. It shall be appreciated that embodiments may be practiced without some or all of these specific details.

FIG. 1 illustrates a front perspective view 100 of a passively vented goggle 102, in accordance with one embodiment.

As seen in FIG. 1, the passively vented goggle 102 comprises a frame 108, a lens 112, one or more posts 104 to retain tear-off layers, an outrigger 114 and a strap 116 which is affixed to the outrigger 114, and one or more inlets 110 along an exterior surface of the frame 108. According to certain embodiments, the one or more inlets 110 are connected to corresponding channels that extend to one or more outlets disposed upon an inner periphery of the frame 108, and behind the lens 112.

Figure 2:
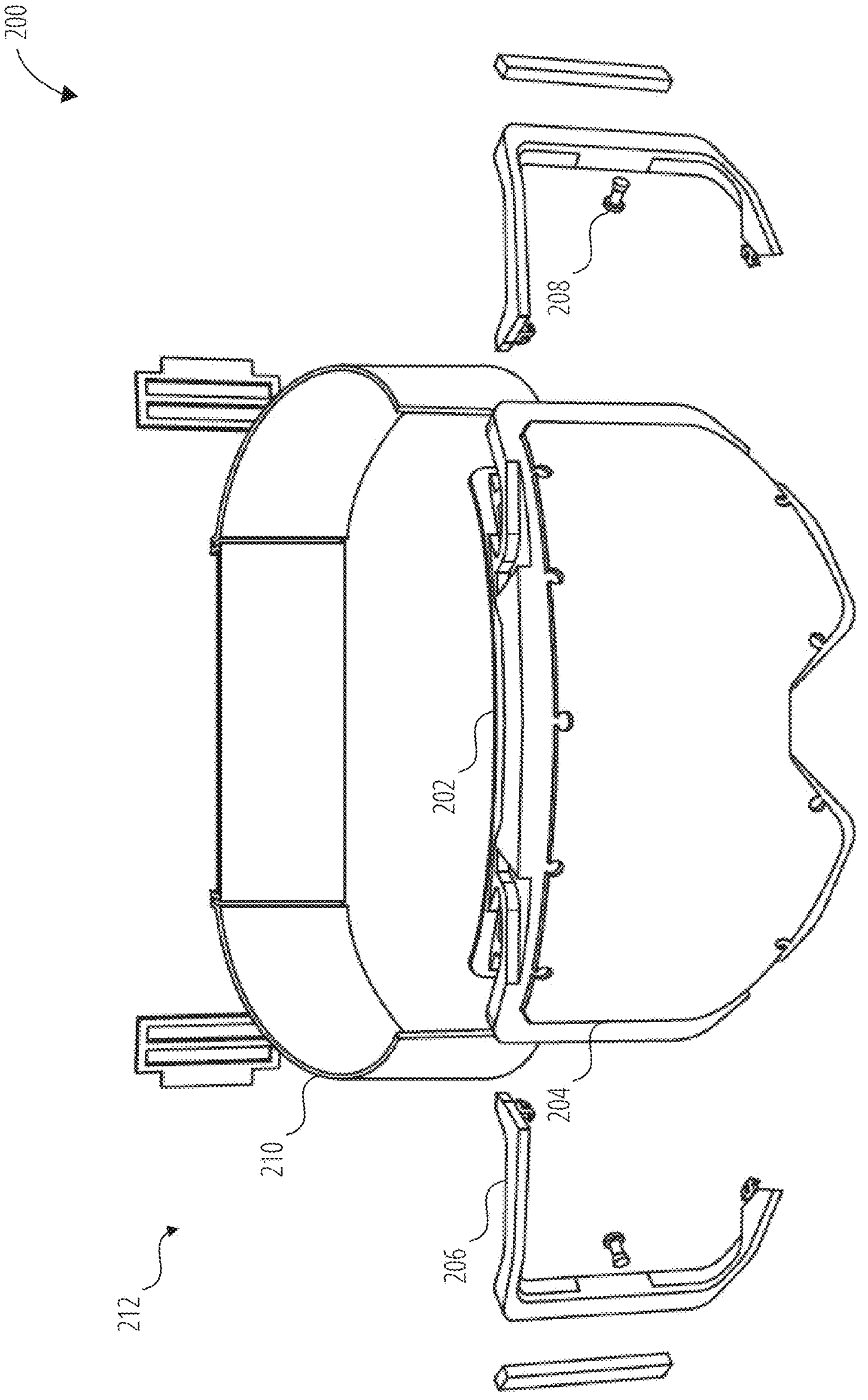
FIG. 2 is a diagram depicting an exploded view of a passively vented goggle, accordance with one embodiment.

FIG. 2 illustrates an exploded view 200 of a passively vented goggle 212, accordance with one embodiment. As seen in the exploded view 200, the passively vented goggle 212 comprises a frame 202, a lens 204, an outrigger 206 configured to retain a strap 210, and one or more posts 208, configured to retain tear-offs.

Figure 3:
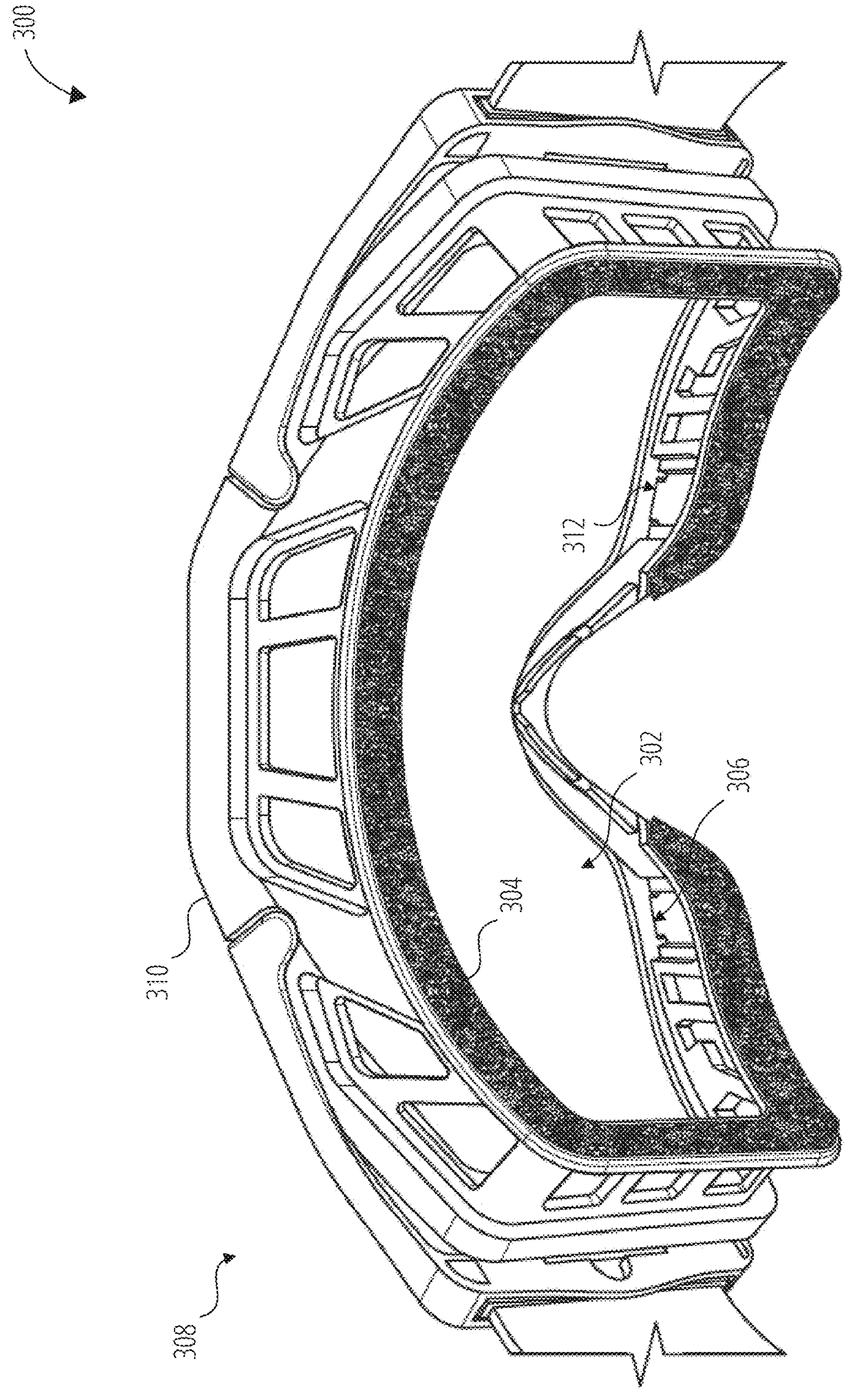
FIG. 3 is a diagram depicting a passively vented goggle, in accordance with one embodiment.

FIG. 3 illustrates a rear perspective view 300 of a passively vented goggle 308, depicting an interior surface of the passively vented goggle 308, in accordance with one embodiment. As seen in the rear perspective view 300, the passively vented goggle 308 comprises a frame 310, a liner material 304 applied upon the interior surface of the frame 310, and wherein the liner material 304 is configured to conform to a shape of a user's face.

According to certain embodiments, and as seen in FIG. 3, the passively vented goggle includes one or more outlets 306 disposed upon the interior surface of the passively vented goggle 308, and behind the lens 302. As discussed above, the one or more outlets 306 may be connected via a channel to the one or more inlets 106 depicted in FIG. 1 and FIG. 2. Accordingly, air flowing through the one or more inlets 106 may pass through a channel to the one or more outlets 306 to the interior surface of the passively vented goggle 308.

In some embodiments, the outlets 306 may include a foam insert 312 that fits within the outlets 306, and which may be held in place by an outlet cover, by one or more barbs or protrusions along a peripheral surface of the outlet 306, or by a suitable adhesive which may be applied to the peripheral surface of the outlet 306. In some embodiments, the foam insert 312 may be interchangeable, such that a user of the passively vented goggle 308 may select a foam insert 312 having a foam density suitable for their given environment or need. For example, a user may select a first foam insert 312 having a higher density for environments with fine dust, or similarly a lighter density foam insert in cleaner environments, to provide greater airflow to the user, thereby increasing comfort.

Figure 4:
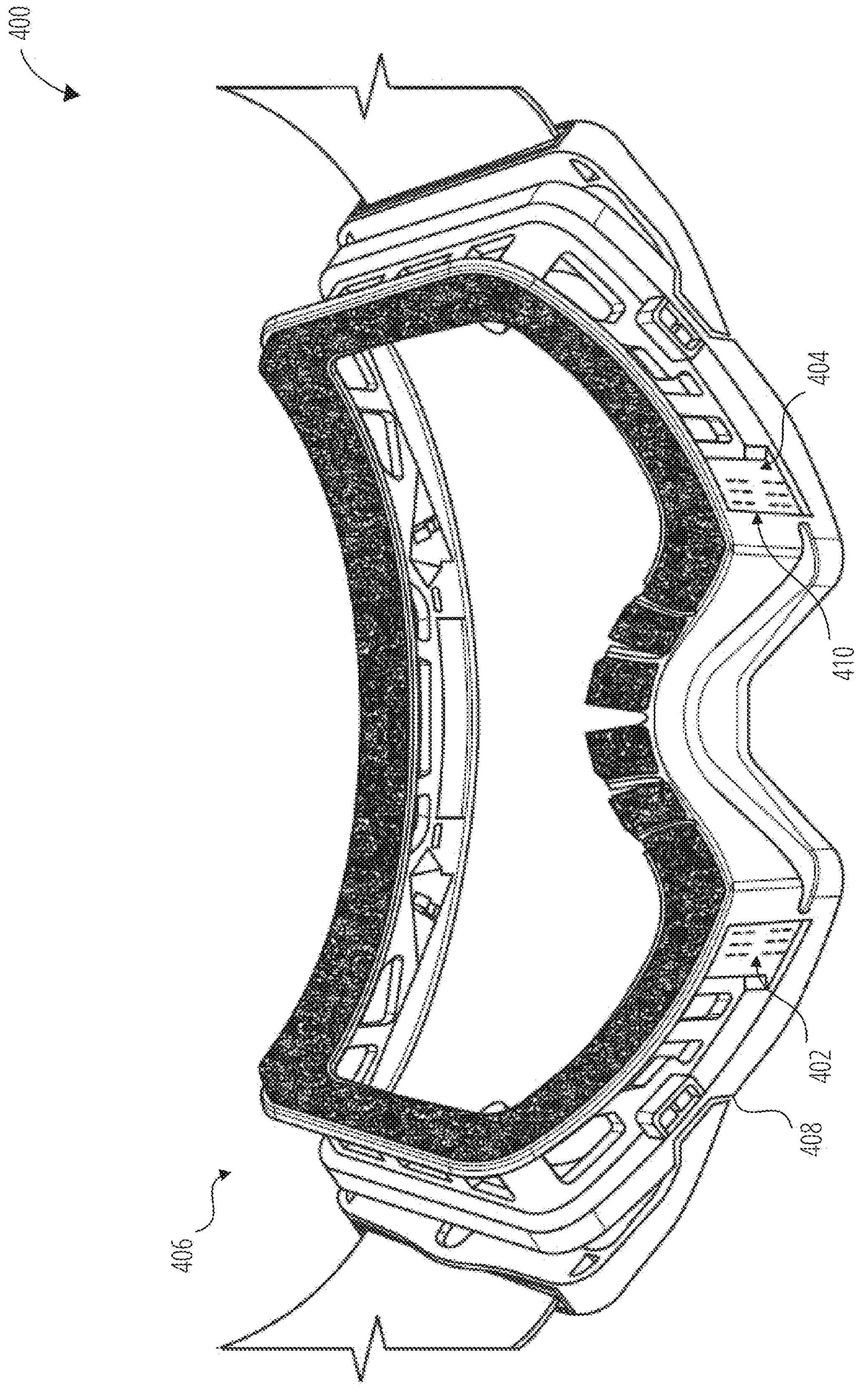
FIG. 4 is a diagram depicting a passively vented goggle, in accordance with one embodiment.

FIG. 4 illustrates a lower rear perspective view 400 of a passively vented goggle 406, in accordance with one embodiment. As seen in the lower rear perspective view 400, inlets are connected to the outlets of the passively vented goggle 212 via channels 402 and 404.

According to certain embodiments, the channels 402 and 404 are formed of an exterior periphery of the frame 408 and a surface of a removable insert, wherein the frame 408 may comprise one or more slots to retain the removable insert. Accordingly, a user may insert the removable insert to form one or more of the channels 402 and 404, or likewise remove the insert to eliminate the channels 402 and 404, thereby causing air flowing into one or more of the inlets disposed upon the exterior surface of the passively vented goggle 406 to be dispersed to the atmosphere from an opening created by the absence of the insert within the lower portion of the passively vented goggle 406.

Figure 5:
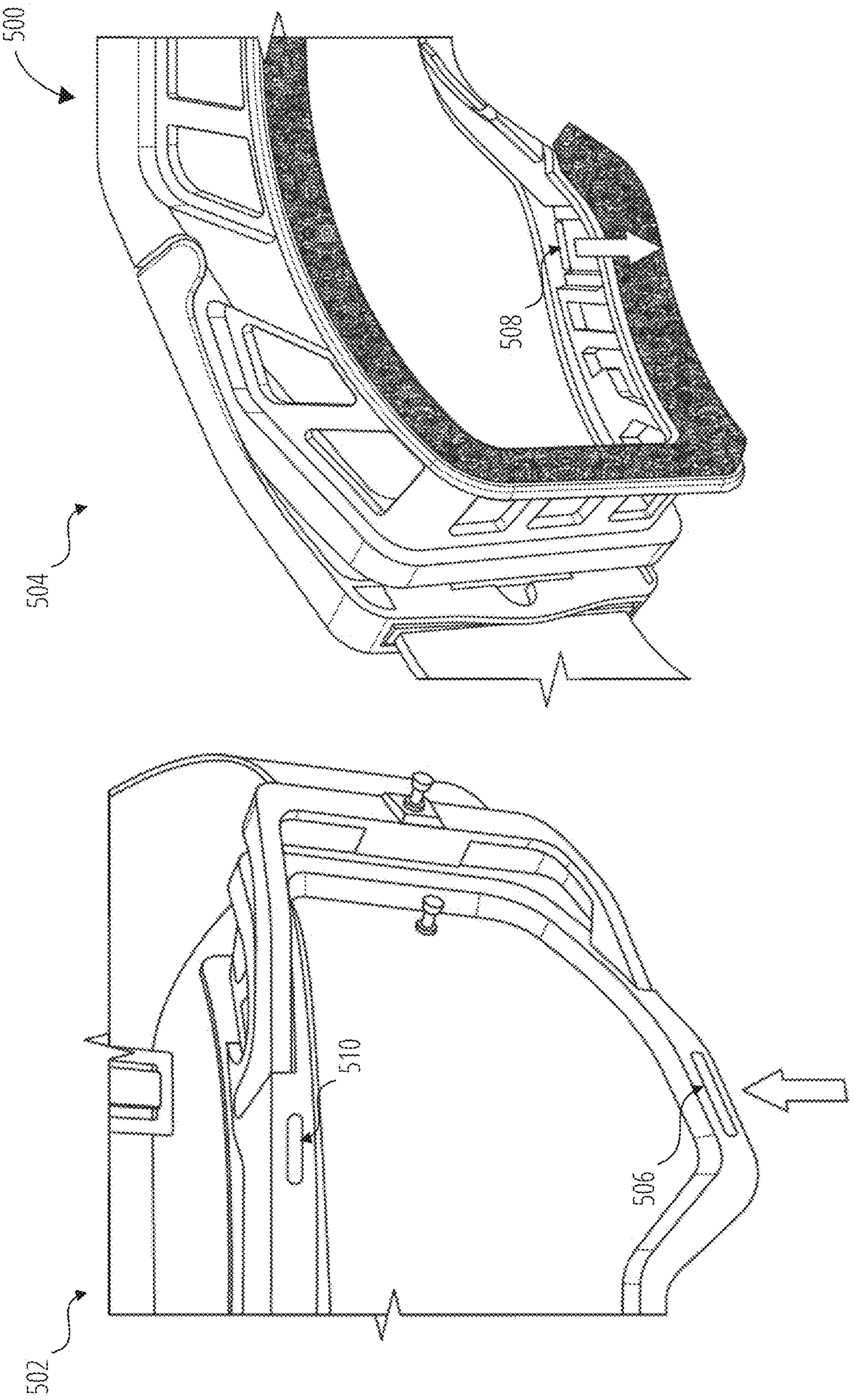
FIG. 5 is a diagram illustrating an inlet and outlet of a passively vented goggle, in accordance with one embodiment.

FIG. 5 is a diagram 500 illustrating an inlet 506 and 510, and outlet 508 of a passively vented goggle, in accordance with one embodiment. The diagram 500 includes a front view 502 of the passively vented goggle, and a rear view 504 of the passively vented goggle.

As seen in the front view 502, air may pass through the inlet 506, passing through a channel (i.e., the channel 402 depicted in FIG. 4), and out of the outlet 508 into the interior of the passively vented goggle 212, as depicted in the rear view 504.

In some embodiments, the outlet 508 may include a cover, wherein the cover may include a removable vented cover (such as the vented cover 410 depicted in FIG. 4). For example, the cover may comprise one or more vents, wherein the vents comprises one or more of: a series of circular holes; a mesh surface; a slatted grill; and an adjustable vent.

Figure 6:
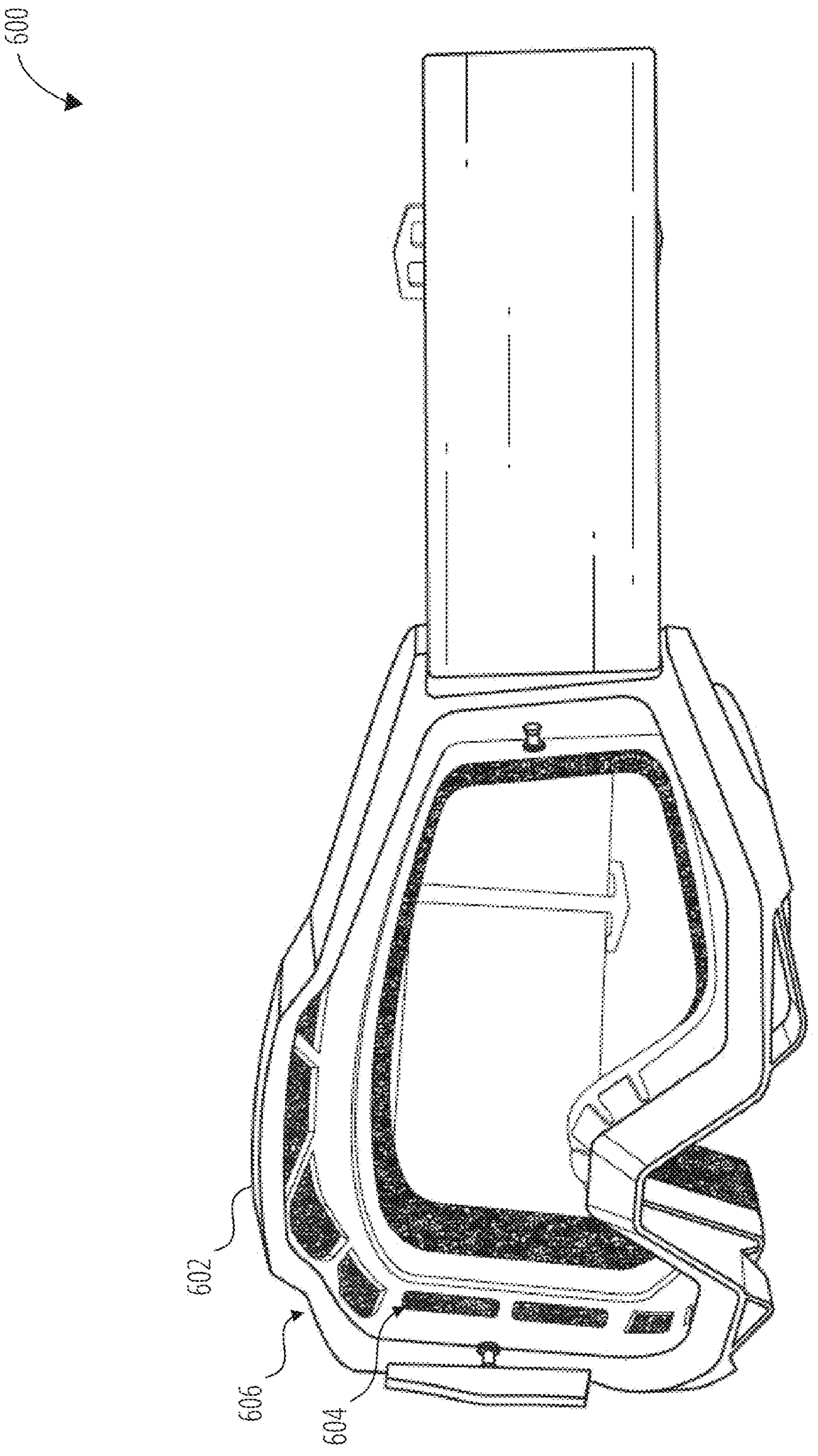
FIG. 6 is a diagram depicting a passively vented goggle, in accordance with one embodiment.

FIG. 6 is a diagram 600 depicting a passively vented goggle 602, in accordance with one embodiment.

According to certain embodiments, the passively vented goggle 602 may include a liner material 602 applied upon the outer periphery of the frame 606. For example, as seen in the diagram 600, the liner material 604 may be applied to the outer periphery of the frame 606, such that an external surface of the passively vented goggles 602 is covered by the liner material 604. In some embodiments, the liner material may comprise a foam liner.

In an embodiment of the invention, the outlet 508 may include a foam insert (such as the foam insert 312 depicted in FIG. 3) that fits within the outlet, and may be held in place by an outlet cover, by one or more barbs or protrusions along a peripheral surface of the outlet 508, or by a suitable adhesive which may be applied to the peripheral surface of the outlet 508. In some embodiments, the foam insert may be interchangeable, such that a user of the goggle 602 may select a foam insert having a foam density suitable for their given environment or need. For example, a user may select a first foam insert having a higher density for environments with fine dust, or similarly a lighter density foam insert in cleaner environments, to provide greater airflow to the user, thereby increasing comfort.

Figure 7:
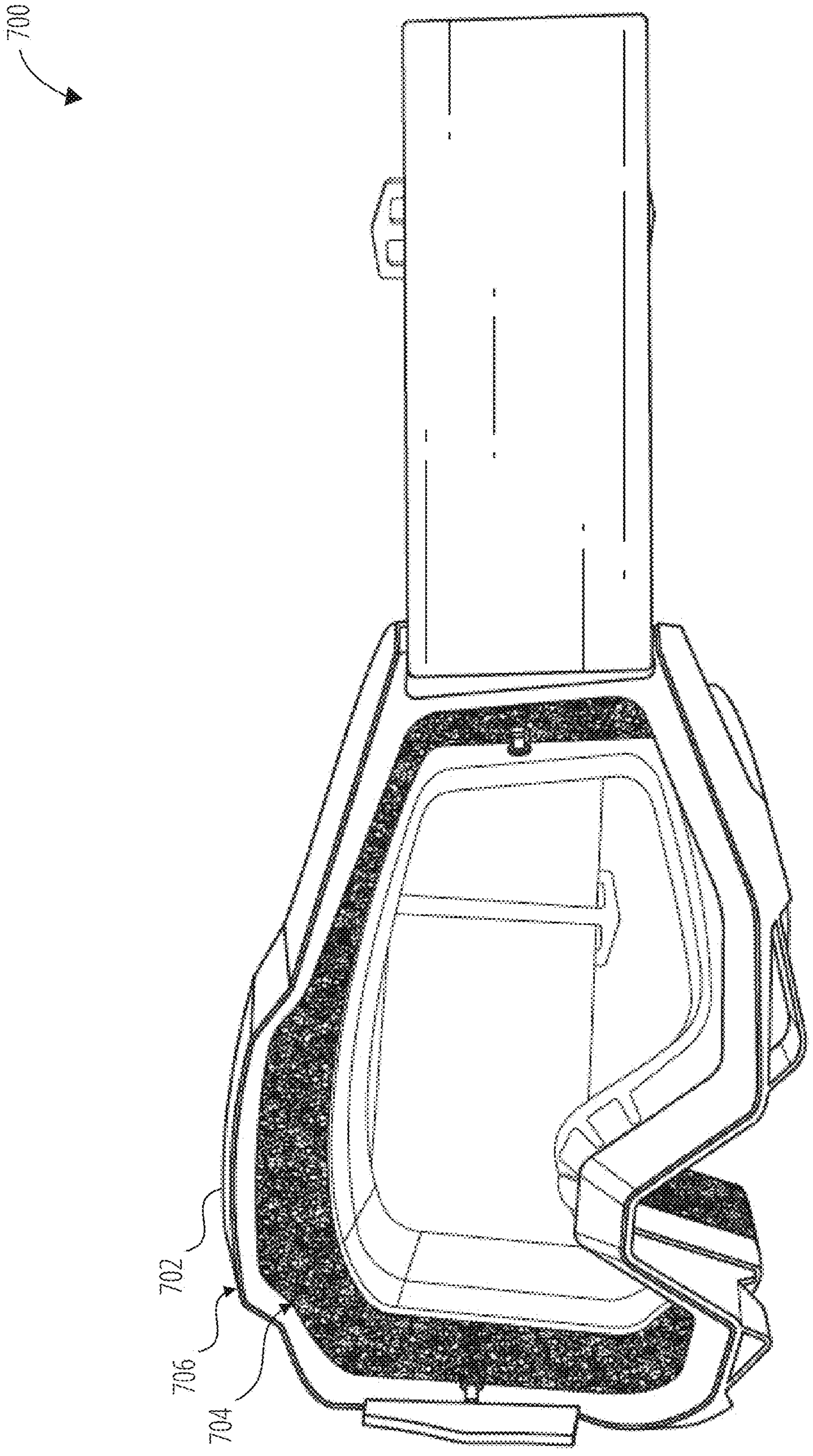
FIG. 7 is a diagram depicting a passively vented goggle, in accordance with one embodiment.

FIG. 7 is a diagram 700 depicting a passively vented goggle 702, in accordance with one embodiment.

According to certain embodiments, the passively vented goggle 702 may include a liner material 704 applied upon the inner periphery of the frame 706. For example, as seen in the diagram 700, the liner material 704 may be applied to the inner periphery of the frame 706, such that an interior surface, include the outlet described in FIG. 3 and FIG. 5, of the passively vented goggles 702 is covered by the liner material 704. In some embodiments, the liner material may comprise a foam liner.

What is claimed is:

1. A goggle comprising:

a frame that comprises a lens aperture, an exterior surface, an interior surface, and an inner periphery, the inner periphery being located between the exterior surface and the interior surface, the exterior surface being configured to be oriented away from a user's face, and the interior surface being configured to be oriented upon the user's face, the frame comprising a slotted mount disposed upon the exterior surface of the frame;

an outrigger mounted upon the exterior surface of the frame via an insert that is pressed into the slotted mount, wherein the outrigger is configured to retain a strap;

a lens mounted upon the exterior surface of the frame and within the lens aperture of the frame, wherein the frame is disposed at least partially around an outer periphery of the lens;

an inlet disposed upon the exterior surface of the frame;

an outlet disposed behind the lens, and upon the inner periphery of the frame, the outlet including an interchangeable foam insert selected from among a plurality of foam inserts that fits within the outlet, the interchangeable foam insert comprising a foam density configured to correspond with an environmental condition, and wherein the interchangeable foam insert is held in place by one or more protrusions along a peripheral surface of the outlet;

an outlet cover to retain the interchangeable foam insert;

a liner material applied to the inner periphery of the frame and covering the outlet disposed behind the lens; and a channel that connects the inlet and the outlet, wherein the channel comprises a duct formed by a surface of the outrigger and the exterior surface of the frame.

2. The goggle of claim 1, wherein the outlet cover comprises a vented cover that comprises one or more of:

a series of circular holes;

a mesh surface;

a slatted grill; and an adjustable vent.

3. The goggle of claim 1, wherein the outlet cover is a removable vented cover.

4. The goggle of claim 1, wherein the inlet comprises a first pair of inlets and a second pair of inlets, and the outlet comprises a first pair of outlets and a second pair of outlets.

5. An eye-protection device comprising:

a frame that comprises a lens aperture, an exterior surface, an interior surface, and an inner periphery, the inner periphery being located between the exterior surface and the interior surface, the exterior surface being configured to be oriented away from a user's face, and the interior surface being configured to be oriented upon the user's face, wherein the frame comprises a slotted mount disposed upon the exterior surface of the frame;

an outrigger mounted upon the exterior surface of the frame via an insert that is pressed into the slotted mount, wherein the outrigger is configured to retain a strap;

a lens mounted upon the exterior surface of the frame and within the lens aperture of the frame, wherein the frame is disposed at least partially around an outer periphery of the lens;

an inlet disposed upon the exterior surface of the frame;

an outlet disposed behind the lens, and upon the inner periphery of the frame, the outlet including an interchangeable foam insert selected from among a plurality of foam inserts that fits within the outlet, the interchangeable foam insert comprising a foam density configured to correspond with an environmental condition, and wherein the interchangeable foam insert is held in place by one or more protrusions along a peripheral surface of the outlet;

an outlet cover to retain the interchangeable foam insert;

a liner material applied to the inner periphery of the frame and covering the outlet disposed behind the lens; and a channel that connects the inlet and the outlet, wherein the channel comprises a duct formed by a surface of the outrigger and the exterior surface of the frame.

6. The eye-protection device of claim 5, wherein the outlet cover comprises a vented cover that comprises one or more of:

a series of circular holes;

a mesh surface;

a slatted grill; and an adjustable vent.

7. The eye-protection device of claim 5, wherein the inlet comprises a first pair of inlets and a second pair of inlets, and the outlet comprises a first pair of outlets and a second pair of outlets.

* * * * *